United States Patent [19]

Hatch, III

[11] 4,299,776

[45] Nov. 10, 1981

[54] PREPARATION OF ESTERS

[75] Inventor: Charles E. Hatch, III, Pennington, N.J.

[73] Assignee: FMC Corporation, Philadelphia, Pa.

[21] Appl. No.: 162,479

[22] Filed: Jun. 24, 1980

Related U.S. Application Data

[63] Continuation-in-part of Ser. No. 102,727, Dec. 13, 1979, abandoned.

[51] Int. Cl.$^3$ .................. C07C 120/00; C07C 121/75
[52] U.S. Cl. ................................................. 260/465 D
[58] Field of Search ................................... 260/465 D

[56] References Cited

U.S. PATENT DOCUMENTS

| | | | |
|---|---|---|---|
| 3,787,477 | 1/1974 | Matthews | 560/124 X |
| 3,835,176 | 9/1974 | Matsuo et al. | 260/465 D |
| 4,024,163 | 5/1977 | Elliott et al. | 260/465 D X |
| 4,113,763 | 9/1978 | Norton | 260/465 D |
| 4,123,451 | 10/1978 | Sheldon et al. | 260/465 D |

FOREIGN PATENT DOCUMENTS

| | | |
|---|---|---|
| 1439615 | 6/1976 | United Kingdom . |
| 2000764 | 1/1979 | United Kingdom . |

OTHER PUBLICATIONS

Francis et al., *J. Chem. Soc.*, 95, 1403 (1909).
Loudon et al., *J. Chem. Soc.*, PT.2, 1780 (1959).
Zymalkowski et al., *Arch. Pharm.*, 290, 218 (1957).

*Primary Examiner*—Dolph H. Torrence
*Attorney, Agent, or Firm*—Richard L. Hansen; Henry R. Ertelt

[57] ABSTRACT

α-cyano esters are prepared by reacting an acyl halide with an aldehyde in a homogeneous mixture of substantially water-miscible aprotic solvent and an aqueous solution of water-soluble cyanide salt.

6 Claims, No Drawings

PREPARATION OF ESTERS

This is a continuation in part of application Ser. No. 102,727, filed Dec. 13, 1979 now abandoned.

This invention relates to a process for preparing esters of carboxylic acids; more specifically, esters which contain a cyano group bonded to the alpha-carbon atom in the alcohol portion of the ester molecule.

Esters with a cyano group so situated are prepared by reacting an acid with the appropriate cyanohydrin. According to U.S. Pat. No. 3,835,176, the reaction can also be effected by treating a mixture of an acyl halide and the appropriate aldehyde, optionally in an aprotic solvent, with aqueous sodium or potassium cyanide. It is disclosed, for example, that 3-phenoxy-α-cyanobenzyl chrysanthemate was prepared in 64% yield by reacting a heterogeneous mixture of chrysanthemoyl chloride, 3-phenoxybenzaldehyde, and aqueous sodium cyanide at 0° C. for 1 hour.

U.S. Pat. No. 4,123,451 discloses the variation of the last described heterogeneous process wherein an aprotic solvent, a water-immiscible aprotic solvent, is added. Using n-heptane, and employing only a trace of water so that solid NaCN was present, the insecticidal ester, α-cyano-3-phenoxybenzyl 3-(2,2-dichloroethenyl)-2,2-dimethylcyclopropanecarboxylate, was prepared in 43% yield in 1 hour and in quantitative yield in 18 hours at room temperature. The insecticidal ester, α-cyano-3-phenoxybenzyl 2-(4-chlorophenyl)-3-methylbutanoate, was similarly prepared in quantitative yield in 1.0 hour. Replacement of the n-heptane with the water-miscible aprotic solvents, 1,4-dioxane or N,N-dimethylformamide, led to yields of no more than 5% of the desired ester. Indeed, a skilled chemist would expect the dissolved water to hydrolyze the acyl chloride, decreasing the yield, when the water and aprotic solvent are miscible.

Were it possible to further shorten the reaction time and increase the yield, producing insecticidal alpha-cyano esters by reacting an acyl halide with an aldehyde and a cyanide salt would be of great commercial interest. Insecticidal alpha-cyano esters whose preparation would be facilitated include α-cyano-3-phenoxybenzyl 3-(2,2-dichloroethenyl)-2,2-dimethylcyclopropanecarboxylate and α-cyano-3-phenoxybenzyl 3-(2,2-dibromoethenyl)-2,2-dimethylcyclopropanecarboxylate, whose insecticidal activity is disclosed in U.S. Pat. No. 4,024,163, incorporated by reference herein. Other insecticidal alpha-cyano esters of particular interest are α-cyano-3-phenoxybenzyl 3-(2-chloro-3,3,3-trifluoropropenyl)-2,2-dimethylcyclopropanecarboxylate, α-cyano-3-phenoxybenzyl 2,2,3,3-tetramethylcyclopropanecarboxylate and α-cyano-3-phenoxybenzyl 2-(4-chlorophenyl)-3-methylbutanoate, whose activity is disclosed in Great Britain Pat. No. 2,000,764, U.S. Pat. 3,835,176, and Great Britain Pat. No. 1,439,615, respectively, all of which are incorporated herein by reference.

One advantage of this invention is that it provides a process for making alpha-cyano esters in very high yield in a short time. Another advantage is that it provides an esterification process whose product does not require lengthy and expensive purification.

Accordingly, this invention provides a method to prepare an insecticidal alpha-cyano ester by reacting an acyl halide with an aldehyde in a homogeneous mixture of substantially water-miscible aprotic solvent and an aqueous solution of water-soluble cyanide salt. Surprisingly, the acyl halide is not appreciably hydrolyzed by the proximate water. Either the acyl halide or the aldehyde may exhibit optical or geometric isomerism, which is not affected by the reaction.

In a preferred embodiment, there is provided a process for preparing an insecticidal α-cyano-3-phenoxybenzyl ester of the formula

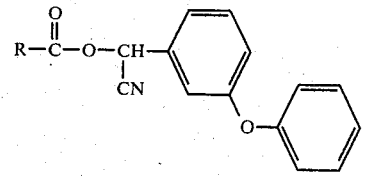

wherein R is selected from the group consisting of 3-(2,2-dichloroethenyl)-2,2-dimethylcyclopropyl, 3-(2,2-dibromoethenyl)-2,2-dimethylcyclopropyl, 3-(2-chloro-3,3,3-trifluoropropenyl)-2,2-dimethylcyclopropyl, 2,2,3,3-tetramethylcyclopropyl, and 1-(4-chlorophenyl)-2-methylpropyl which comprises reacting an acyl halide of the formula

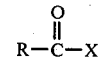

wherein X is chlorine or bromine and R is as defined above with 3-phenoxybenzaldehyde in a homogenous mixture of substantially water-miscible aprotic solvent and an aqueous solution of water-soluble cyanide salt. It is especially preferred that R be selected from 3-(2,2-dichloroethenyl)-2,2-dimethylcyclopropyl, 3-(2,2-dibromoetheny)-2,2-dimethylcyclopropyl, 3-(2-chloro-3,-3,3-trifluoropropenyl)-2,2-dimethylcyclopropyl, and 1-(4-chlorophenyl)-2-methylpropyl.

although the process of this invention is especially advantageous when R is selected from the groups named above, the process is also effective in producing other alpha-cyano esters wherein R is an aliphatic or aromatic group, which may optionally contain various substituents. Although the process of this invention is prefereably employed to produce α-cyano-3-phenoxybenzyl esters by using 3-phenoxybenzaldehyde as a reactant, the process is equally suited to the production of other alpha-cyano esters by varying the type of aldehyde employed in the process. Although the process employs an acyl halide as one of the reactants, preferably an acyl chloride, another reactive acid derivative, such as an anhydride, may be substituted for the acyl halide.

Various substantially water-miscible aprotic solvents may be employed in the process. Tetrahydrofuran, acetonitrile, 1,4-dioxane, N,N-dimethylformamide, and diethylene glycol dimethyl ether are suitable. Among these, tetrahydrofuran is preferred. Other useful solvents include dimethylsulfoxide, nitromethane, pyridine, hexamethylphosphoramide, N-methylpyrrolidone, sulfolane, and dimethylacetamide. Any of the aforesaid solvents may be used singly or in combination with each other.

A number of water-soluble cyanide salts may be used; for example, the salt may be an alkali metal cyanide such as lithium, sodium, potassium rubidium, or cesium cyanide, or mixtures thereof. Among these, sodium cyanide is preferred, since it is readily available and inexpensive. The cyanide salt is generally employed in excess molar amount, the molar ratio of the cyanide salt to the aldehyde lying in the range 1.2–1.6, preferably about 1.5–1.6.

The cyanide salt is dissolved in a mixture of substantially water-miscible aprotic solvent and water. In general, the ratio, on a volume basis, of aprotic solvent to water is in the range 0.25–6, preferably 0.5–5, most preferably about 2.0.

Aproximately equimolar amounts of the acyl halide and the aldehyde should be used, with the molar ratio of acyl halide to aldehyde in the rane 0.9–1.3, preferably about 1.1–1.2.

The process is carried out by mixing the ingredients, maintaining the temperature of the reactants between $-20°$ C. and 60° C., preferably about between 40° C. and 50° C., and stirring the reactants until the process is complete, the course of the reaction being conveniently followed by gas liquid partition chromatography (glpc).

The process of this invention will be clarified by reference to the following Examples which illustrate it. In the Examples, temperatures are in degrees Celsius.

Example 1

PREPARATION OF
α-CYANO-3-PHENOXYBENZYL
3-(2,2-DICHLOROETHENYL)-2,2-DIMETHYLCYCLOPROPANECARBOXYLATE

A. Using Tetrahydrofuran (1) Sodium cyanide (0.765 g, 15.6 mmole), along with 20 ml of 2:1 tetrahydrofuran:water by volume, was charged to a reaction flask, and the resultant solution was stirred while the temperature was raised to 40°. 3-Phenoxybenzaldehyde (2.06 g, 10 mmole) was added in 5 ml of the tetrahydrofuran/water mixture (25 ml total). 3-(2,2-Dichloroethenyl)-2,2-dimethylcyclopropanecarbonyl chloride (2.84 g, 12.5 mmole) was then added to the flask dropwise over a 10 minute period. The temperature of the reaction mixture was maintained between 40° and 40° during the acyl chloride addition. The reaction mixture was then stirred at 40° for an additional 2 hours, after which it was extracted three times with 15 ml portions of n-heptane. The combined organic phases were washed once with water (15 ml), once with a 2 N aqueous sodium hydroxide solution (15 ml), three more times with water (15 ml) portions), dried over magnesium sulfate, filtered, and concentrated under reduced pressure. A quantitative yield of α-cyano-3-phenoxybenzyl 3-(2,2-dichloroethenyl)-2,2-dimethylcyclopropanecarboxylate remained as the residue.

(2) To a stirred solution of sodium cyanide (2.40 g, 0.049 mole) in a 1:1 by volume mixture of water and tetrahydrofuran (50 ml) at 15° was added dropwise over 30 minutes a mixture of 3-phenoxybenzaldehyde (7.00 g, 0.035 mole) and 3-(2,2-dichloroethenyl)-2,2-dimethylcyclopropanecarbonyl chloride (10.00 g, 0.042 mole). Stirring was continued at 15° for an additional 2 hours, after which the reaction mixture was extracted thrice with methylene chloride (40 ml each). The combined organic layers were washed once with aqueous 2 N NaOH (50 ml), four times with waer (50 ml portions) to a final wash pH of about 6, then dried over MgSO4 and concentrated to give α-cyano-3-phenoxybenzyl 3-(2,2-dichloroethenyl)-2,2-dimethylcyclopropanecarboxylate (13.9 g, 95.5% yield).

(3) To a stirred solution of sodium cyanide (0.74 g, 0.015 mole) in a 1:1 by volume mixture of water and tetrahydrofuran (20 ml) at 30° was added all at once 3-phenoxybenzaldehyde (1.98 g, 0.01 mole) in the same solvent system (5 ml) followed by a dropwise addition over 10 min of (1R,3R)-3-(2,2-dichloroethenyl)-2,2-dimethylcyclopropanecarbonyl chloride (2.73 g, 0.012 mole). Stirring was continued at 30° for an additional 2 hours, after which the mixture was cooled to room temperature and extracted thrice with heptane (25 ml each). The combined organic layers were washed once with aqueous 2 N NaOH (25 ml), then four times with water (25 ml each) to a final wash pH of about 6, dried over Na2SO4, and concentrated to give (R,S)-α-cyano-3-phenoxybenzyl (1R,3R)-3-(2,2-dichloroethenyl)-2,2-dimethylcyclopropanecarboxylate (3.79 g, 91% yield).

(4) Sodium cyanide (0.74 g, 0.015 mole) and 20 ml of the solvent, which was varied as shown below, were charged to a 50 ml round bottom flask equipped with a dropping funnel. After bringing the flask contents to the desired reaction temperature, 3-phenoxybenzaldehyde (1.98 g, 0.010 mole) in 5 ml of the solvent was added to the flask. 3-(2,2-Dichloroethenyl)-2,2-dimethylcyclopropanecarbonyl chloride (2.73 g, 0.012 mole) was then added dropwise under a nitrogen atmosphere to the stirred flask contents over a period of 30 minutes. After complete addition, the readtion mixture was stirred at the desired reaction temperature for 2 hours. The reaction mixture was then worked up by extracting it three times with 25 ml portions of heptane. The combined extracts were washed twice with 25 ml portions of aqueous 2 N hydrochloric acid, then twice with 25 ml portions of aqueous 2 N sodium hydroxide, and finally with water, before drying the organic phase over sodium sulfate. After removing the solvent by evaporation, the residul α-cyano-3-phenoxybenzyl 3-(2,2-dichloroethenyl)-2,2-dimethylcyclopropanecarboxylate was weighed and analyzed by gas-liquid partition chromatography for purity, permitting calculation of the chemical yield as the weight yield multiplied by the purity. The results of these experiments appear in Table 1.

TABLE 1

| Solvent Composition (v/v) | Reaction Temperature | Chemical Yield |
|---|---|---|
| Water* | 0° | 7% |
| Water* | 30° | 12% |
| 1/5 THF/Water* | 30° | 23% |
| ⅓THF/Water | 30° | 74% |
| 1/1 Water/THF | 0° | 98% |
| 1/1 THF/Water | 30° | 92% |
| 2/1 THF/Water | 30° | 88% |
| 5/1 THF/Water | 30° | 92% |
| 0.1% Water in THF$^a$* | 0° | 3% |
| 0.1% Water in THF$^a$* | 30° | 5% |

*Not within the scope of this invention $^a$Solid NaCN was present

B. Using Dioxane (1) A reaction flask, charged with 25 ml 1,4-dioxane and a solution of sodium cyanide (2.4 g, 0.049 mole) in 25 ml water, was cooled to 0°. To the flask was added 3-phenoxybenzaldehyde (7 g, 0.035 mole) in one portion, with stirring. 3-(2,2-Dichloroethenyl)-2,2-dimethylcyclopropanecarbonyl chloride (10 g, 0.042 mole) was added dropwise over a period of 30 minutes. The temperature of the mixture was maintained between 0° and 5°, and stirring was continued for one hour after the acyl chloride had been added. The reaction mixture was then extracted three times with 50 ml portions of diethyl ether. After phase separation, the combined organic layers were washed once with a 2 N aqueous sodium hydroxide solution, three times with 50 ml portions of water, dried over magnesium sulfate, and concentrated under reduced pressure to afford α-cyano-3-phenoxybenzyl 3-(2,2-dichloroethenyl)-2,2-dimethylcyclopropanecarboxylate (11.8 g, 81% yield).

(2) When the above process was varied by using 0.056 mole sodium cyanide, 0.049 mole of the acyl halide, a temperature of 15°, and the mixture was stirred for 2 hours after the acyl chloride had been added, 13.8 g of the desired ester was obtained (94.5% yield).

C. Using Acetonitrile

To a stirred solution of sodium cyanide (0.74 g, 0.015 mold) in a 1:1 by volume mixture of water and acetonitrile (20 ml) at room temperature was added all at once 3-phenoxybenzaldehyde (1.98 g, 0.01 mole) in the same solvent system (5 ml) followed by a dropwise addition over 10 minutes of cis-3-(2,2-dichloroethenyl)-2,2-dimethylcyclopropanecarbonyl chloride (2.73 g, 0.012 mole). Stirring was continued at room temperature for 2 hours, after which the mixture was extracted thrice with methylene chloride (30 ml each). The combined organic layers were washed once with aqueous 2 N NaOH (25 ml), then thrice with water (25 ml each) to a final wash pH of about 6, dried over Na$_2$SO$_4$, and concentrated to give α-cyano-3-phenoxybenzyl cis-3-(2,2-dichloroethenyl)-2,2-dimethylcyclopropanecarboxylate (3.76 g, 90% yield).

D. Using Dimethylformamide

3-Phenoxybenzaldehyde (1.98 g, 0.010 mole) was added in one portion to a stirred solution of sodium cyanide (0.69 g, 0.014 mole) in dimethylformamide/water (20 ml/20 ml). 3-(2,2-Dichloroethenyl)-2,2-dimethylcyclopropanecarbonyl chloride was then added dropwise over 15 minutes to the stirred reaction mixture. After the addition, the reaction mixture was stirred at room temperature for two hours and then extracted with ether (50 ml). The ethereal solution was washed once with a 1 N solution of aqueous sodium hydroxide, three times with water (25 ml) and dried over anhydrous sodium sulfate. Evaporation of the solvent afforded α-cyano-3-phenoxybenzyl 3-(2,2-dichloroethenyl)-2,2-dimethylcyclopropanecarboxylate; 62% pure by glpc.

E. Using Diethylene Glycol Dimethyl Ether

A reaction flask was cooled to 0° and charged with 20 ml of diethylene glycol dimethyl ether/water solution (1/1 by volume) and sodium cyanide (0.78 g, 0.016 mole). The resultant solution was stirred, and 3-phenoxybenzaldehyde (1.98 g, 0.01 mole) was added in 5 ml of diethylene glycol dimethyl ether. 3-(2,2-Dichloroethenyl)-2,2-dimethylcyclopropanecarbonyl chloride (2.73 g, 0.012 mole) was added dropwise to the stirred reaction mixture at 20° over a 10 minute period. Stirring was continued for 2 hours. The reaction mixture was then extracted three times with 15 ml portions of diethyl ether, once with 15 ml of water, once with a 2 N solution of aqueous sodium hydroxide, three times with water (15 ml), dried over magnesium sulfate, and concentrated under reduced pressure to afford α-cyano-3-phenoxybenzyl 3-(2,2-dichloroethenyl)-2,2-dimethylcyclopropanecarboxylate (4.35 g, 90% pure glpc).

EXAMPLE 2

PREPARATION OF α-CYANO-3-PHENOXYBENZYL 3-(2,2-DIBROMOETHENYL)-2,2-DIMETHYLCYCLOPROPANECARBOXYLATE

Sodium cyanide (0.80 g, 0.016 mole) was charged to a reaction vessel together with 25 ml of a mixture of water and tetrahydrofuran (1/1 by volume). 3-Phenoxybenzaldehyde (2.31 g, 0.012 mole) in 10 ml of water/tetrahydrofuran solution (1/1 by volume) was then added in one portion, and 3-(2,2-dibromoethenyl)-2,2-dimethylcyclopropanecarbonyl chloride (4.4 g, 0.014 mole) was added dropwise over a 15 minute period. The reaction mixture was stirred for 2 hours at 20°, and the desired ester (6.97 g, 86% pure by glpc) was isolated as described in Example 1E. EXAMPLE 3

PREPARATION OF α-CYANO-3-PHENOXYBENZYL 2,2,3,3-TETRAMETHYLCYCLOPROPANECARBOXYLATE

This ester was prepared by the method of Example 1B.2), substituting 2,2,3,3-tetramethylcyclopropanecarbonyl chloride as the acyl halide and stirring the mixture for 3 hours after addition of the acyl chloride. The residual oil remaining after solvent evaporation weighed 3.11 g; glpc analysis indicated the oil was 41.5% α-cyano-3-phenoxybenzyl 2,2,3,3-tetramethylcyclopropanecarboxylate.

EXAMPLE 4

PREPARATION OF α-CYANO-3-PHENOXYBENZYL 2-(4-CHLOROPHENYL)-3-METHYLBUTANOATE

A. Using Tetrahydrofuran

To a stirred solution of sodium cyanide (0.74 g, 0.015 mole) in a 1:1 by volume mixture of water and tetrahydrofuran (20 ml) at 30° was added all at once 3-phenoxybenzaldehyde (1.98 g, 0.01 mole) in the same solvent system (5 ml), followed by the dropwise addition of 2-(4-chlorophenyl)-3-methylbutanoyl chloride (2.77 g, 0.012 mole). Stirring was continued at 30° for an additional 2 hours, after which the mixture was cooled to room temperature and extracted thrice with heptane (25 ml each). The combined organic layers were washed once with aqueous 2 N NaOH (25 ml), then four times with water (25 ml each) to a final wash pH of about 6, dried over Na$_2$SO$_4$, and concentrated to give the desired product (3.90 g, 93% yield). When the experiment was repeated under substantially the same conditions the weight yield was 91%.

B. Using Dioxane

Sodium cyanide (0.74 g, 0.015 mole) and 20 ml of the solvent, which was varied as shown below, were charged to a 50 ml round bottom flask, and 3-phenoxybenzaldehyde (1.98 g, 0.010 mole) in 5 ml of the solvent was added. With the stirred flask contents at 30°, 2-(4-chlorophenyl)-3-methylbutanoyl chloride (2.77 g, 0.012 mole) was added dropwise under nitrogen over a 30 minute period. Following the addition, the reaction mixture was stirred at 30° for 2 hours, and then worked up as follows. After the addition of 25 ml of water, the flask contents were extracted three times with 25 ml portions of heptane. The combined extracts were washed twice with 25 ml portions of aqueous 2 N hydrochloric acid, twice with 25 ml portions of aqueous 2 N sodium hydroxide, and then with water, before being dried over sodium sulfate. After removal of the heptane by evaporation, the residual α-cyano-3-phenoxybenzyl 2-(4-chlorophenyl)-3-methylbutanoate was weighed, and the purity was determined by glpc, permitting calculation of the chemical yield as the weight yield times the purity. The results of these experiments appear below in Table 2.

TABLE 2

| Solvent Composition (v/v) | Chemical Yield |
|---|---|
| Water* | 12% |
| 1/1 dioxane/water | 76% |
| 0.1% water in dioxane*a* | 46% |

*Not within the scope of this invention
*a*Solid sodium cyanide was present

EXAMPLE 5

PREPATION OF
α-CYANO-3-PHENOXYBENZYL
3-(2-CHLORO-3,3,3-TRIFLUOROPROPHENYL)-2,2-DIMETHYLCYCLOPROPANECARBOXY-LATE

To a stirred solution of sodium cyanide (0.74 g, 0.015 mole) in a 1:1 by volume mixture of water and tetrahydrofuran (20 ml) at 30° was added all at once 3-phenoxybenzaldehyde (1.98 g, 0.01 mole) in the same solvent system (5 ml), followed by a dropwise addition over 10 minutes of 3-(2-chloro-3,3,3-trifluoropropenyl)-2,2-dimethylcyclopropanecarbonyl chloride (2.60 g, 0.012 mole). Stirring was continued at 30° for an additional 2 hours, after which the mixture was cooled to room temperature and extracted thrice with heptan (25 ml each). The combined organic layers were washed once with aqueous 2 N NaOH (25 ml), then four times with water (25 ml each) to a final wash pH of about 6, dried over Na₂SO₄, and concentrated to give the desired product (3.86 g, 95% yield).

I claim:
1. A process for preparing an insecticidal α-cyano-3-phenoxybenzyl ester of the formula

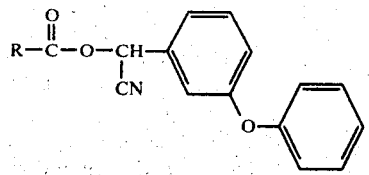

wherein R is selected from the group consisting of 3-(2,2-dichloroethenyl)-2,2-dimethylcyclopropyl, 3-(2,2-dibromoethenyl)-2,2-dimethylcyclopropyl, 3-(2-chloro-3,3,3-trifluoropropenyl)-2,2-dimethylcyclopropyl, and 1-(4-chlorophenyl)-2-methylpropyl which comprises reacting an acyl halide of the formula

wherein X is chlorine or bromine and R is as defined above with b 3-phenoxybenzaldehyde and dissolved water-soluble cyanide salt in a mixture of substantially water-miscible aprotic solvent and water in a ratio of about 0.25–6.

2. The process of claim 1 wherein the water-miscible aprotic solvent is selected from tetrahydrofuran, acetonitrile, 1,4-dioxane, N,N-dimethylformamide, and diethylene glycol dimethyl ether.

3. The process of claim 2 wherein the water-miscible aprotic solvent is tetrahydrofuran.

4. The process of claim 1 wherein the water-soluble cyanide salt is selected from lithium, sodium, potassium, rubidium, or cesium cyanide.

5. The process of claim 4 wherein the water-soluble cyanide salt is sodium cyanide.

6. A process according to any one of claims 1, 2, 3, 4, or 5 wherein the acyl halide is 3-(2,2-dichloroethenyl)-2,2-dimethylcyclopropanecarbonyl chloride.

* * * * *

UNITED STATES PATENT AND TRADEMARK OFFICE
CERTIFICATE OF CORRECTION

PATENT NO. : 4,299,776
DATED : November 10, 1981
INVENTOR(S) : Charles E. Hatch, III It is certified that error appears in the above—identified patent and that said Letters Patent is hereby corrected as shown below:

Col. 2, line 39, "although" should read --Although--;
line 45, "prefereably" should read --preferably--;
line 66, "potassium" should read --potassium,--.
Col. 3, line 40, "40° and 40°" should read --40° and 48°--;
line 46, the "(" between "ml" and "portions" should be deleted.
Col. 4, line 25, "readtion" should read --reaction--;
line 34, "residul" should read --residual--.
Col. 5, line 16, "mold" should read --mole--;
line 21, "cis" should be underlined to read --cis--;
line 29, "cis" should be underlined to read --cis--;
line 68, "pure glpc" should read --pure by glpc--.
Col. 6, line 17, "EXAMPLE 3" should be moved down one line.
Col. 7, line 25, "TRIFLUOROPROPHENYL" should read --TRIFLUOROPROPENYL--;
line 37, "heptan" should read --heptane--.
Col. 8, line 24, "b" should be deleted.

Signed and Sealed this

Twenty-fifth Day of May 1982

[SEAL]

Attest:

GERALD J. MOSSINGHOFF

Attesting Officer

Commissioner of Patents and Trademarks